United States Patent
Hoffman et al.

(10) Patent No.: US 8,427,020 B2
(45) Date of Patent: Apr. 23, 2013

(54) BLOWER ASSEMBLY WITH INTEGRAL INJECTION MOLDED SUSPENSION MOUNT

(75) Inventors: Leslie Hoffman, Tarzana, CA (US); Raymond Lathrop, Northridge, CA (US)

(73) Assignee: CareFusion 212, LLC, San Diego, CA (US)

( * ) Notice: Subject to any disclaimer, the term of this patent is extended or adjusted under 35 U.S.C. 154(b) by 1266 days.

(21) Appl. No.: 11/786,976

(22) Filed: Apr. 13, 2007

(65) Prior Publication Data

US 2007/0247009 A1    Oct. 25, 2007

Related U.S. Application Data

(60) Provisional application No. 60/793,433, filed on Apr. 20, 2006.

(51) Int. Cl.
H02K 5/24 (2006.01)
F04B 35/04 (2006.01)

(52) U.S. Cl.
USPC ...... 310/89; 310/51; 417/423.14; 417/423.15

(58) Field of Classification Search .......... 310/51, 310/89; 248/603, 604; 415/213.1; 417/363, 417/423.14, 423, 15
See application file for complete search history.

(56) References Cited

U.S. PATENT DOCUMENTS

| | | | |
|---|---|---|---|
| 1,491,736 A * | 4/1924 | Polk | 417/363 |
| 2,670,896 A * | 3/1954 | Ardito | 417/363 |
| 3,508,842 A | 4/1970 | Lievens | |
| 4,161,667 A * | 7/1979 | Buckman et al. | 310/51 |
| 4,164,690 A * | 8/1979 | Muller et al. | 318/400.41 |
| 4,933,584 A * | 6/1990 | Harms et al. | 310/162 |
| 6,002,185 A | 12/1999 | Nakao et al. | 310/43 |
| 6,036,456 A * | 3/2000 | Peters et al. | 417/423.3 |
| 6,488,475 B2 * | 12/2002 | Murata et al. | 417/32 |
| 6,490,752 B2 * | 12/2002 | Kushida et al. | 15/319 |
| 6,551,074 B2 | 4/2003 | Kudo et al. | 417/354 |
| 6,617,721 B1 | 9/2003 | Neal | 310/68 |
| 6,960,854 B2 * | 11/2005 | Nadjafizadeh et al. | 310/89 |
| 7,012,346 B2 | 3/2006 | Hoffman et al. | 310/43 |
| 2005/0058556 A1 * | 3/2005 | Cremer et al. | 417/363 |
| 2006/0138878 A1 * | 6/2006 | Hoffman et al. | 310/43 |
| 2006/0213516 A1 | 9/2006 | Hoffman | 128/204.18 |
| 2007/0247009 A1 * | 10/2007 | Hoffman et al. | 310/51 |

FOREIGN PATENT DOCUMENTS

| | | |
|---|---|---|
| DE | 4232851 A1 | 4/1993 |
| DE | 9311489 U1 | 10/1993 |
| DE | 29818179 U1 | 2/1999 |
| EP | 0091228 A | 10/1983 |
| FR | 2811156 A | 1/2002 |
| GB | 2260861 * | 4/1993 |
| JP | 4-325855 * | 11/1992 |
| JP | 07274438 | 10/1995 |
| WO | WO 2005/091469 A1 | 9/2005 |

* cited by examiner

Primary Examiner — Tran Nguyen
Assistant Examiner — Terrance Kenerly
(74) Attorney, Agent, or Firm — McDermott Will & Emery LLP (57) ABSTRACT

A blower assembly comprises a blower housing having a stator assembly integrally formed therewith. The stator assembly includes a stator bore having a rotor magnet rotatable therewithin such that the motor assembly is configured as a brushless D.C. motor. An impeller is mounted on a motor shaft of the motor assembly and has a plurality of vanes extending upwardly therefrom. Each one of the vanes has a vane height which is optimized to minimize the formation of fluid eddy losses during compression of air by the impeller. A bearing assembly rotatably coupling the rotor magnet to the stator assembly is sized and configured to maintain an air gap of approximately 0.0002 inches between the vanes and a housing interior surface of the blower housing during rotation of the impeller.

7 Claims, 6 Drawing Sheets

BLOWER ASSEMBLY WITH INTEGRAL INJECTION MOLDED SUSPENSION MOUNT

CROSS-REFERENCE TO RELATED APPLICATIONS

The present application claims priority to U.S. Provisional Application No. 60/793,433 filed on Apr. 20, 2006, the entire contents of which is expressly incorporated by reference herein. The present application is also related to U.S. Utility patent application Ser. No. 11/128,552 entitled PORTABLE CONTINUOUS POSITIVE AIRWAY PRESSURE SYSTEM filed on May 13, 2005, and to U.S. Utility patent application Ser. No. 11/649,674 entitled USER INTERFACE AND HEAD GEAR FOR A CONTINUOUS POSITIVE AIRWAY PRESSURE DEVICE filed on Jan. 4, 2007, the entire contents of each being expressly incorporated by reference herein.

STATEMENT RE: FEDERALLY SPONSORED RESEARCH/DEVELOPMENT (Not Applicable)

BACKGROUND

The present invention relates generally to patient ventilation systems and, more particularly, to a motor blower assembly incorporating an improved brushless D.C. motor assembly of reduced size and which is configured to rotatably drive a precision impeller with minimal variations in an air gap between the rotating impeller and the blower housing such that the blower assembly operates with improved efficiency.

The impeller includes a plurality of vanes that are optimized to improve the flow capability of the blower assembly with a reduced amount of power consumption at the motor assembly. Advantageously, because of its small size, low weight and reduced output of noise, vibration and heat, the blower assembly is suitable for use in sensitive environments such as in a hospital room or bedroom of a respiratory care patient undergoing continuous positive airway pressure (CPAP) treatment.

Brushless D.C. motors are known to operate at a relatively high levels of efficiency under low-load conditions as compared to conventional (brushed) D.C. motors. Furthermore, brushless D.C. motors are known to generate a reduced amount of noise as compared to brushed D.C. motors. As such, brushless D.C. motors are well-suited for use in relatively small or miniaturized fans or blower assemblies such as may be used as for cooling purposes and/or for generating compressed air.

Examples of blower assemblies include that which is disclosed in U.S. Pat. No. 4,164,690 issued to Muller et al. which describes a compact miniature fan such as may be used for cooling electronic components. The miniature fan of the Muller reference includes a radial fan wheel disposed within a housing and which is mounted to a rotor of a motor assembly. The motor assembly is configured as a stator mounted on a base plate of the housing. The rotor is secured to an underside of the impeller and rotates about the motor shaft.

Although the miniature fan of the Muller reference is disclosed as having a relatively small size of about 23 mm in height and 73 mm in width, the miniature fan is not believed to be suitable for certain applications such as in a CPAP device which requires an even smaller size and lower-weight blower assembly. Furthermore, the configuration of the radial fan wheel as used in the Muller reference is not understood to possess the ability to produce the required compressive flow at a high efficiency level. Furthermore, the miniature fan as used in the Muller reference is not understood to operate at a reduced noise level and with reduced vibration output as is required in a portable CPAP device.

U.S. Pat. No. 6,551,074 issued to Kudo et al. discloses a centrifugal fan having an electric motor and an impeller mounted on the electric motor. The centrifugal fan draws air into one side of a housing of the fan and discharges the air out of the housing in a radial direction. The electric motor includes a stator which has a stator-side magnetic pole and a rotor which rotates about the stator. The impeller includes a plurality of blades which draw air into the axial side of the fan.

Unfortunately, the blades in the fan of the Kudo reference form a relatively large air gap with the housing such that, during operation, the fan is believed to generate fluid eddies as a result of air flowing between the air gap. The fluid eddies are believed to interfere with the aerodynamic efficiency of the compressed air flowing through the vanes toward the outlet. In addition, the reduced aerodynamic efficiency of the fan is believed to result in a concomitant increase in noise such that the Kudo device is also not believed to be suitable for use in a portable CPAP device.

As can be seen, there exists a need in the art for a miniaturized blower assembly incorporating a brushless D.C. motor capable of operating at high efficiency in compressing air and which has a reduced noise, vibration and heat output during its operation such that the blower assembly is mountable upon or adjacent to a patient such as in a portable or wearable CPAP device. More specifically, there exists a need in the art for a blower assembly wherein the impeller is capable of rotating in close proximity to a housing of the blower assembly in order to minimize the formation of fluid eddies which could otherwise compromise the compressive efficiency of the blower assembly and which may contribute to the generation of excessive noise and vibration by the blower assembly.

Furthermore, there exists a need in the art for a blower assembly which is mountable in such a manner as to minimize the outwardly-directed radiation of structure-borne vibration as sound. Additionally, there exists a need in the art for a blower assembly that is mountable in such a manner as to attenuate or reduce the transmission of vibration to a patient undergoing respiratory treatment such as CPAP therapy. Finally, there exists a need in the art for an economical process for producing a blower assembly with relatively small tolerances in order to provide the desirable qualities of high operating efficiency and reduced noise and vibration output.

BRIEF SUMMARY

The above-mentioned deficiencies and drawbacks associated with blower assemblies of the prior art are specifically addressed and alleviated by the blower assembly of the present invention which, in one aspect, comprises a blower housing incorporating a brushless D.C. motor assembly. The motor assembly comprises a stator assembly and a rotor magnet that is rotatable within the stator assembly on a bearing assembly coupling the rotor magnet to the stator assembly.

The blower assembly includes a blower housing having an annular blower inlet disposed on an axial end of the blower assembly and a blower outlet extending tangentially from a radial side of the blower assembly. The blower housing preferably comprises upper and lower housing portions which are engageable to one another at a perimeter joint and which collectively form an annular chamber or volute defining a housing interior surface.

The stator assembly may be joined to or integrally formed with the lower housing portion and has a stator bore within which the rotor assembly is rotatably mountable. In an exemplary embodiment, the motor assembly is configured as three-slot/two-pole brushless D.C. motor assembly. In such a configuration, the stator assembly comprises three core sections each having a winding extending therearound and which are sequentially magnetizable during rotation of the rotor by the application of current applied from an external power source.

The rotor magnet is preferably configured as a permanently magnetized magnet preferably having opposing poles and which is mountable on a motor shaft. The rotor magnet is operative to magnetically interact with the stator assembly for inducing rotation of the motor shaft and, hence, a centrifugal impeller mounted on the motor shaft. The motor shaft has distal and proximal ends and defines a shaft axis. A shaft shoulder is formed on the motor shaft adjacent the distal end. The impeller is configured to be mountable such as via press fit on the proximal end of the motor shaft. In one embodiment, the impeller includes a hub portion, a circumferential ramp portion and a plurality of vanes extending upwardly from the ramp portion.

The hub portion optionally has a rounded or dome shape similar to that which is disclosed in commonly-owned PCT Application No. WO 2005/091469. The ramp portion is preferably conically shaped and extends outwardly from the hub portion. The vanes extend upwardly from the ramp portion and are disposed in spaced relation to one another on the ramp portion. Preferably, the vanes are non-radially oriented and may be oriented to be afterward-facing in relation to a rotational direction of the impeller.

Each one of the vanes has a vane height which is optimized such that during rotation of the impeller, aerodynamic losses are minimized. Such aerodynamic losses may occur due to the formation of fluid eddies as air inducted into the blower assembly is compressed by the impeller. In one embodiment of the blower assembly, the vane height is optimized such that the blower assembly produces a flow rate of up to approximately 125 liters per minute at a pressure of approximately 20 cm $H_2O$ using less than approximately 15 watts of input power at the motor assembly.

Furthermore, the blower assembly is configured such that the impeller rotates within relatively close proximity to the housing interior surface in order to further enhance the compressive efficiency of the impeller. In this regard, each one of the vanes defines an air gap between the free edge of the vane and the housing interior surface. The blower assembly and, more particularly, the bearing assembly is configured such that the air gap is maintained at less than approximately 0.0006 inches during rotation of the impeller and preferably, is maintained at approximately 0.0002 inches. The maintenance of the relatively small air gap minimizes vane-to-vane leakage as air is compressed by the blower assembly.

The impeller may include a downwardly turned ring portion which extends about a periphery of the ramp portion and which may facilitate unobstructed flow from the impeller vanes to the circumferential volute or annular chamber of the blower housing. In addition, the ring portion provides an optimal location on the impeller from which material may be removed in order to statically and dynamically balancing the impeller. Because the impeller is fixedly coupled to the rotor magnet and bearing assembly, balancing of the impeller results in a balancing of the rotatable components of the motor assembly such that a minimal mount of vibration is produced by the blower assembly.

The blower assembly is configured such that the bearing assembly is removably mountable within the stator bore. As was mentioned above, the bearing assembly is specifically configured to rotatably couple the motor shaft to the stator assembly. The bearing assembly comprises upper and lower bearings each including inner and outer bearing races interconnected by ball bearings. The upper and lower bearings are disposed in spaced axial relation to one another in order to maximize the moment arm about which the motor shaft is supported. The moment arm provided by the bearing assembly thereby minimizes lateral movement of the motor shaft axis relative to a stator axis defined by the stator bore.

The ramp portion, upper housing portion, and adjacent pairs of vanes define a plurality of vane passages each having a vane inlet and a vane outlet. As was earlier mentioned, the vanes have a vane height which is optimized to prevent formation of fluid eddies and noise-generating vortices in the vane passages. Furthermore, the blower housing is configured in a modular aspect wherein the combination of the upper housing portion and impeller are interchangeable with an impeller and upper housing portion of a different configuration such that different flow characteristics are producible by the blower assembly using a baseline stator assembly.

For example, the upper housing portion is configurable in alternative (e.g., larger) cross-sections in order to provide an annular chamber having a different cross-section and thereby resulting in different flow characteristics of the blower assembly. In this same regard, the impeller is configurable in differing vane heights and with free edges that are formed complimentary to the upper housing portion to maintain the relatively small air gap and thereby minimize vane-to-vane aerodynamic losses.

The blower housing preferably includes at least one, and more preferably, three suspension mounts extending laterally outwardly from the blower housing. The suspension mounts are preferably sized and configured to support the blower housing. Importantly, each of the suspension mounts is specifically configured to attenuate vibration (e.g., radial and axial vibration) generated during operation of the impeller. Furthermore, the suspension mounts may be tailored with a specific size and configuration in order to maximize the attenuation (i.e., tune the suspension mounts) of vibration within a specific frequency range.

The suspension mounts may be tuned to attenuate vibration in proportion to the mass and resonant frequency of a specific blower assembly configuration. Each one of the suspension mounts is preferably configured as a serpentine spring member extending outwardly from the blower housing and having a free end which is configured to interconnect or mount the blower assembly to a mounting frame such as an outer housing of a CPAP device. In addition, the suspension mounts are preferably positioned adjacent to the perimeter joint and are integrally formed with at least one of the upper and lower housing portions such as by injection molding.

BRIEF DESCRIPTION OF THE DRAWINGS

These and other features of the present invention will become more apparent upon reference to the drawings wherein.

DETAILED DESCRIPTION

Referring now to the drawings wherein the showings are for purposes of illustrating preferred embodiments of the present invention and not for purposes of limiting the same, shown in FIGS. 1-10 is a blower assembly 10 which is specifically configured to provide a relatively high flow rate at relatively high pressure while consuming relatively little input power. The blower assembly 10 is configured in a relatively small size having a short axial height small diameter but which is capable of producing a relatively high flow rate of compressed with minimal output of vibration, noise and heat. In this regard, the blower assembly 10 is particularly well-suited for use in sensitive applications such as in a portable or wearable continuous positive airway pressure (CPAP) device similar to that which is disclosed in U.S. application Ser. No. 11/649,674 entitled User Interface and Headgear for a Continuous Positive Airway Pressure Device, the entire contents of which is incorporated by reference herein.

As will be described in greater detail below, the blower assembly 10 efficiently produces the above-mentioned flow characteristics by employing an impeller 56 having a plurality of vanes 64, 66 that are optimized to produce a flow rate of up to approximately 125 liters per minute at a pressure of up to approximately 20 cm $H_2O$ using less than about 15 watts of input power. The vanes 64, 66 of the impeller 56 collectively form a plurality of vane passages which compress the air while minimizing the formation of fluid eddies in the vane passages. In addition, as indicated above, the blower assembly 10 is specifically adapted to generate a minimal amount of vibration due to the precision impeller 56 achievable with static and dynamic balancing. Furthermore, the blower assembly 10 is configured such that, during rotation of the impeller 56, the vanes 64, 66 rotate in extremely close proximity to the blower housing 12 in order to minimize vane-to-vane leakage which otherwise reduces efficiency in compressing the air.

In another aspect of the invention, the blower assembly 10 may be mountable in a mounting frame 120 (e.g., on an outer housing 124 of a CPAP device 126) in an arrangement that minimizes the transmission of vibration and which may be otherwise radially-outwardly directed from the blower assembly 10 as sound. More specifically, the blower assembly 10 may be provided with a plurality of suspension mounts 108 which extend laterally outwardly from the blower housing 12 and by which the blower assembly 10 is supported such as in the mounting frame 120 of the above-mentioned CPAP device 126.

In addition, the blower assembly 10 is specifically configured to be producible in an economical manner due to the optional use of injection molding to integrally fabricate major components of the blower assembly 10. In this regard, the blower housing 12 may be fabricated of upper and lower housing portions 14, 16. The stator assembly 32 may be integrally molded with the lower housing portion 14. The combination of the upper housing portion 16 and impeller 56 may be substituted with a different upper housing portion 16 and impeller 56 combination to provide alternative flow characteristics as will be described in greater detail below.

Referring more particularly now to FIGS. 1-6, shown is the blower assembly 10 in a preferred embodiment incorporating an exemplary D.C. brushless motor assembly 30 specifically configured such that the blower assembly 10 has a relatively short axial length (i.e., height) and a relatively small overall diameter. The miniaturized or compact configuration of the blower assembly 10 is due in part to the mounting of a permanently magnetized rotor magnet 106 within the stator assembly 32 as opposed to an arrangement wherein the rotor magnet 106 assumes a ring shape and is disposed radially outwardly relative to the stator assembly 32 as disclosed and illustrated in commonly owned U.S. Pat. No. 7,012,346, issued to Hoffman et al. In this regard, it should be noted that certain aspects and features of the present invention are not limited solely to the exemplary embodiments illustrated herein but are further applicable to conventional brushed D.C. motors as well as other motor arrangements. In addition, other novel features of the present invention as will be described in greater detail below are also applicable to alternative centrifugal blower arrangements other than that which is described in detail below and illustrated in the figures.

Referring to FIGS. 1-6, the blower assembly 10 comprises the blower housing 12 having the stator assembly 32 disposed therewithin. As was mentioned above, the rotor magnet 106 is preferably rotatably coupled to the stator assembly 32 such as by means of a bearing assembly 86. The multi-vane impeller 56 is fixedly mounted such as by press fit on a motor shaft 78 and rotates with the rotor magnet 106. The impeller 56 draws air into an annular blower inlet 20 defined by an upper housing neck 104 and a hub portion 60 of the impeller 56. Air is drawn into the blower inlet 20 in an axial direction whereupon the vanes 64, 66 compress the air in the annular chamber 24 or volute as defined by the blower housing 12. The compressed air is discharged out of the blower housing 12 at a blower outlet 22 in a radial direction.

Figure 6:
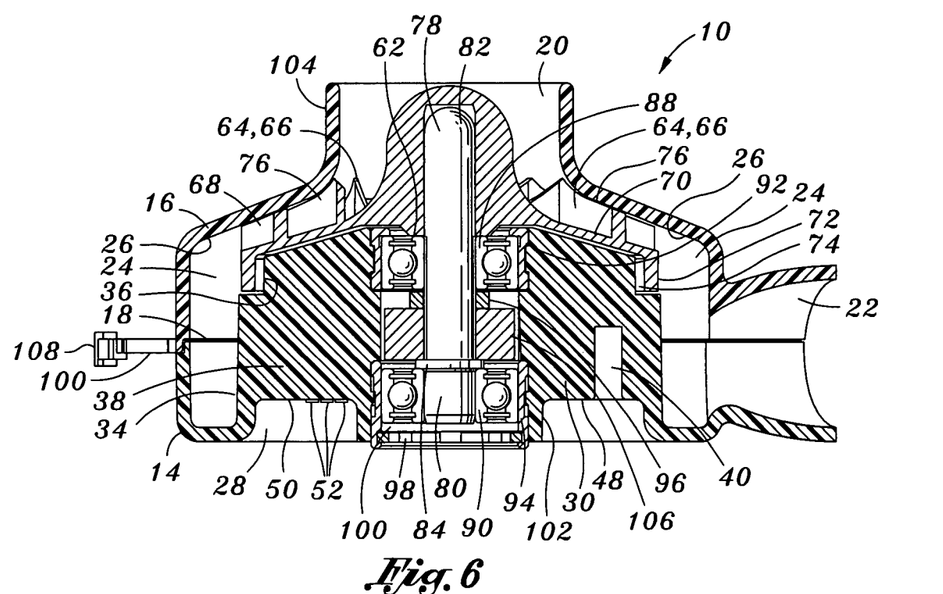
FIG. 6 is a cross-sectional view taken along lines 6-6 of the blower assembly of FIG. 5 and further illustrating the motor assembly comprising the stator assembly and the rotor magnet rotatable therewithin.
Figure 7:
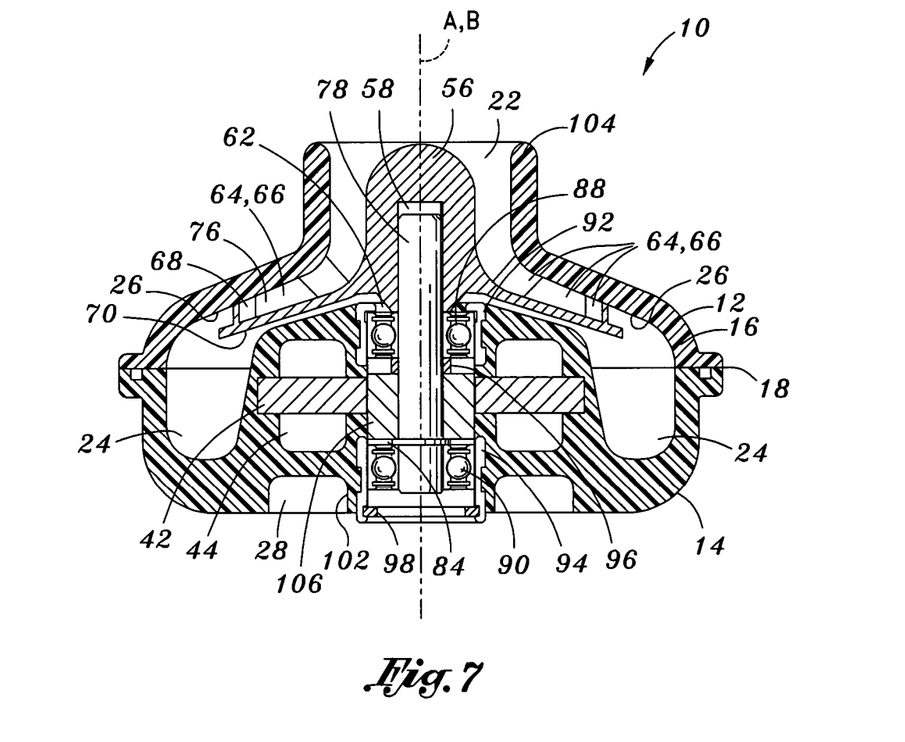
FIG. 7 is a cross-sectional view of the blower assembly illustrating the impeller and blower housing in an alternative embodiment.

Referring particularly to FIGS. 6-7, the motor assembly 30 comprises the stator assembly 32 and rotor magnet 106 rotatable within a stator bore 38 of the stator assembly 32. In an exemplary embodiment, the motor assembly 30 is configured as a three-slot/two-pole brushless D.C. motor assembly 30 wherein each of the slots of the stator assembly 32 are arranged circumferentially to define a number of rotor teeth or core sections 42 each having layer(s) of electrical winding 44 wound thereabout. It should be noted that the stator assembly 32 is not limited to the three-slot arrangement illustrated in the figures but may be provided with any number of slots (i.e., core sections 42) with the rotor magnet 106 being provided with a complimentary number of poles.

The brushless D.C. motor assembly 30 illustrated in the figures may include an intelligent electronic controller which is operative to sequentially commutate or provide current to the core sections 42 of the stator assembly 32 at the appropriate time to thereby induce rotation of the rotor magnet 106. In this regard, the motor assembly 30 may further include a means for sensing the position and/or orientation of magnetic poles 46 of the rotating rotor magnet 106. A position sensor 48 may be provided in the form of Hall sensors which cooperate with the controller in order to regulate the speed of the motor assembly 30.

Figure 4:
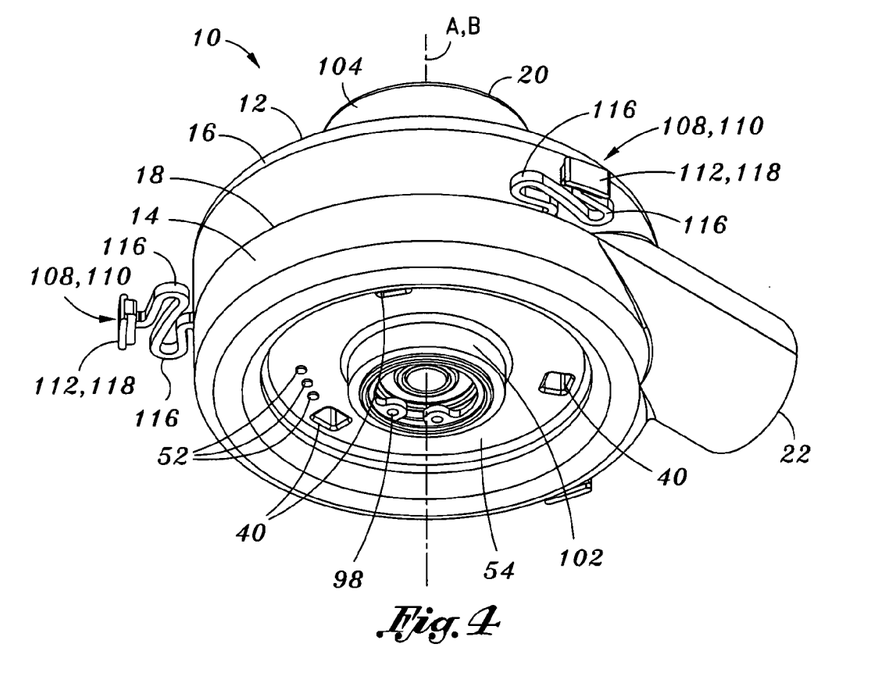
FIG. 4 is a perspective view of the blower assembly looking at an underside thereof and illustrating the retainer element in the installed position.

Referring briefly to FIG. 4, the controller may be mounted on a printed circuit board 54 (PCB) and may include electrical contacts 52 for connecting to and controlling the motor assembly 30. In addition, the controller may be integrated with the PCB 54 which may further include the position sensors 48 (e.g., Hall sensors) to sense the relative positions and speed of the magnetic poles 46 of the rotor magnet 106 relative to the stator assembly 32. The blower housing 12 is configured such that the PCB 54 is located within an annular recess 28 disposed on an underside of a lower housing portion 14 as best seen in FIGS. 4 and 6.

Referring to FIGS. 1-7, the blower housing 12 comprises the lower housing portion 14 which is configured to be fixedly secured to the upper housing portion 16 such that the upper and lower housing portions 14, 16 collectively define the blower housing 12. The upper and lower housing portions 14, 16 may be secured to one another along the perimeter joint 18 such as by adhesive bonding, sonic welding or other suitable means including mechanical attachment. Advantageously, forming of the upper housing portion 16 as a separate component from the lower housing portion 14 provides a semi-modular aspect to the blower assembly 10 in that an upper housing portion having a differing configuration (i.e., a different cross-sectional shape) may be mated to a baseline configuration of the lower housing portion 14.

As was earlier mentioned, the lower housing portion 14 may be integrally formed with the stator assembly 32. In this manner, the blower assembly 10 may be configured to provide differing flow characteristics using the baseline lower housing portion 14/stator assembly 32 by substituting an impeller 56 and upper housing portion 16 having an alternative configuration to achieve an increase in flow rate or pressure at the blower outlet 22. Also facilitating the semi-modular aspect of the blower assembly 10 is the exteriorly accessible location of the PCB 54 on the underside of the blower housing 12 which allows for convenient substitution of a controller and/or commutator 50 of alternative configuration and having operating characteristics that are complementary to the new upper housing portion 16 and impeller 56.

As was mentioned above and as illustrated in FIG. 6, the stator assembly 32 is preferably, but optionally, integrally formed with the lower housing portion 14. In this regard, the stator assembly 32 and lower housing portion 14 may be fabricated by injection molding as a unitary structure. The plurality of the core sections 42 and associated windings 44 which comprise the stator assembly 32 are contained within a stator housing 34 which is integral with the lower housing portion 14. Toward this end, a plurality of housing apertures 40 may be strategically located in the stator assembly 32 so as to eliminate warpage that may occur due to uneven shrinkage or contraction of the molded structure during cooling of the stator assembly 32/lower housing portion 14 after the injection molding process.

The housing apertures 40 are sized and positioned in order to eliminate the occurrence of any overly thick sections which may contract or shrink to a greater extent than other molded portions of the stator assembly 32/lower housing portion 14. In this manner, the combination of the lower housing portion 14/stator assembly 32 may be fabricated with precise dimensional control which facilitates final assembly with other components of the blower assembly 10. Furthermore, by precisely controlling the dimensional characteristics of the blower assembly 10 during injection molding of the lower housing portion 14/stator assembly 32, substitution of a different (i.e., larger) upper housing portion 16 and complimentary impeller 56 facilitates bonding of the upper and lower housing portions 14, 16 at the perimeter joint 18. In addition, controlling the injection molding process (e.g., shrinkage) also minimizes problems associated with maintaining the relatively narrow air gap 76 between the rotating impeller 56 and the housing interior surface 26 especially considering the relatively high speed (i.e., up to 35,000 RPM) at which the blower assembly 10 may be operated.

Referring still to FIGS. 6-7, the stator assembly 32 may incorporate the bearing assembly 86 during the manufacturing process. In the interest of manufacturing economy and dimensional precision, upper and lower bearing carriers 92, 94 may be integrally molded with the stator assembly 32/lower housing portion 14 by positioning the upper and lower bearing carriers 92, 94 within an injection mold (not shown) in such a manner as to maintain precise alignment of the impeller 56 relative to the housing interior surface 26. As illustrated in FIGS. 6-7, the upper and lower bearing carriers 92, 94 are disposed in space relation on upper and lower ends of the stator assembly 32 and may be provided as separate components or may be integrally formed with the stator housing 34.

The upper and lower bearings 88, 90 which are preferably over-sized in relation to the inertial and rotational loads imposed by the rotating impeller 56. In this regard, by providing the upper and lower bearing 90 in a relatively large size, wear on the upper and lower bearings 88, 90 over time is minimized such that the useful life of the blower assembly 10 is extended. Furthermore, the use of over-sized upper and lower bearings 88, 90 facilitates the substitution of a larger-sized impeller 56 as may be desired in order to increase the flow capacity of the blower assembly 10. The use of over-sized upper and lower bearings 88, 90 also minimizes the loss in operating efficiency of the blower assembly 10 and minimizes the development of greater levels of vibration and/or noise as may otherwise occur over time due to normal wear and tear.

Referring to FIGS. 1, 2 and 6-7, assembly and disassembly of the blower assembly 10 as may be desired for repair or periodic maintenance is conveniently facilitated by the connectivity of the components. For example, the bearing assembly 86 and rotor magnet 106 are easily removable from an underside of the blower housing 12 by disengaging a retainer element 98 best shown in FIG. 4. The retainer element 98 may be configured as a simple snap ring engaged to a corresponding groove formed in a radial lower housing flange 102 extending axially downwardly from the lower housing portion 14. Preferably, a biasing element 100 is interposed between the retainer element 98 and the lower bearing 90 in order to upwardly bias the bearing assembly 86, rotor magnet 106 and, hence, the motor shaft 78. As can be seen in FIGS. 6-7, the motor shaft 78 rotatably couples the rotor magnet 106 and impeller 56 to the bearing assembly 86.

Furthermore, the motor shaft 78 defines a shaft axis B and includes distal and proximal ends 80, 82. The motor shaft 78 also preferably includes a shaft shoulder 84 disposed adjacent the distal end 80 to provide a surface against which the rotor magnet 106 may bear on one side of the shaft shoulder 84 and against which the lower bearing 90 assembly 86 may bear on an opposing side of the shaft shoulder 84. A spacer 96 may be interposed between the rotor magnet 106 and the upper bearing 88 assembly 86. The biasing element 100 is preferably configured as a wave spring although the biasing element 100 may be provided in various other arrangements such as in the form of a compression spring or coil spring.

Regardless of its configuration, the biasing element 100 bears against the retainer element 98 (i.e., snap ring) and pushes upwardly against an outer bearing race of the lower bearing 90 such that the lower bearing 90 is biased upwardly against the upper bearing carrier 92. Each one of the upper and lower bearings 88, 90 is comprised of inner and outer bearing races which are interconnected by a plurality of ball bearings and which allow relative rotational movement of the inner and outer bearing races. As can be seen in FIG. 6, the upper and lower bearings 88, 90 are disposed in spaced axial relation to one another on opposing sides of the rotor magnet 106 in order to maximize the wheelbase or spacing therebetween in order to better resist lateral movement of the motor shaft 78. More specifically, the spacing between the upper and lower bearings 88, 90 is maximized in order to better maintain coaxial alignment of the motor shaft 78 axis with the stator axis A of the stator assembly 32.

Figure 1:
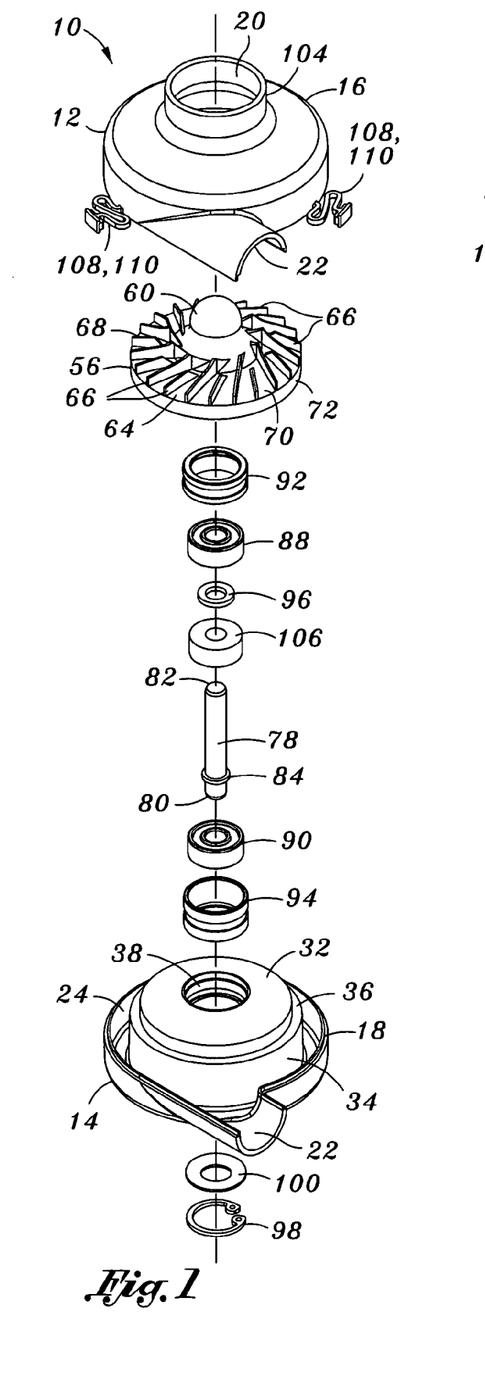
FIG. 1 is an exploded perspective view of a blower assembly illustrating a blower housing have a motor assembly disposed therewithin and including an impeller rotatable with the motor assembly and further illustrating the blower housing having three suspension mounts extending laterally outwardly therefrom.

Referring more particularly now to FIGS. 1, 6 and 7, the impeller 56 is specifically adapted to be mountable on a proximal end 82 of the motor shaft 78. The impeller 56 includes a rounded or domed shaped hub portion 60 having an impeller bore 58 extending at least partially therethrough as best seen in FIG. 6. A conically shaped ramp portion 70 extends circumferentially around the hub portion 60. As can be seen in FIG. 6, the ramp portion 70 is disposed in close rotating relationship with an upper surface of the stator assembly 32 in order to minimize total volume occupied by the impeller 56.

Figure 5:
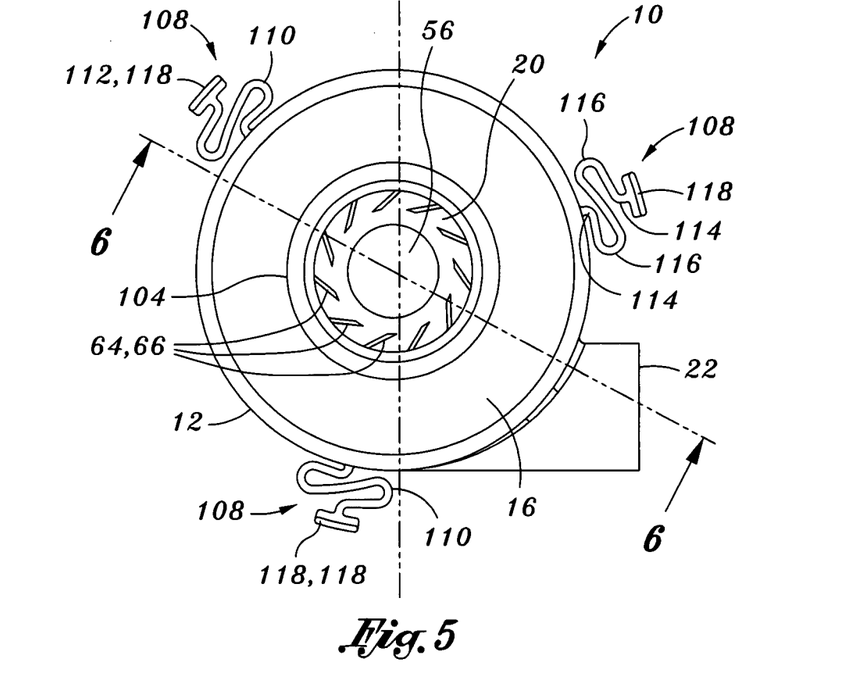
FIG. 5 is a top view of the blower assembly illustrating a plurality of vanes mounted on the impeller.

Notably, the impeller 56 includes a plurality of elongate vanes 64, 66 extending upwardly from the ramp portion 70 with the vanes 64, 66 being disposed in spaced relationship to one another on the ramp portion 70. Furthermore, the vanes 64, 66 are illustrated as being non-radially oriented. More specifically, the vanes 64, 66 are generally aft facing in that the outer edges of the vanes 64, 66 are oriented in a direction opposite the rotational direction of the impeller 56 as best seen in FIG. 5.

The vanes 64, 66 are preferably configured between alternating full-length vanes 66 and partial-length vanes 64 in order to minimize the generation of pressure pulsations at the outer perimeter which can occur in relatively small blowers having a limited quantity of vanes. However, in the blower assembly 10 illustrated and described herein, by alternating partial-length vanes 64 with full-length vanes 66, the overall area at the blower inlet 20 through which air may pass is maximized while pressure pulses are minimized at an opposite end due to an effective increase in the quantity of vanes 64, 66 at an outlet end of the vane passages.

Referring still to FIGS. 6 and 7, each of the vanes 64, 66 has a free edge 68 which itself defines an edge contour. In this regard, each of the vanes 64, 66 has a vane height which is optimized to minimize the formation of fluid eddies. Such fluid eddies may be characterized as aerodynamic losses or energy losses occurring in conventional centrifugal blowers as air inducted into the blower inlet 20 is compressed by the impeller 56. As is known in the art, the pressure and flow rate capability of centrifugal blowers is limited at least in part by the generation of parasitic fluid eddies present to some degree between adjacent vanes of an impeller. Also well know is that fluid eddies can reduce blower efficiency and may generate unwanted acoustic energy (i.e., noise). Although an increase in input power at the motor assembly 30 can overcome losses resulting from fluid eddies, a point is reached wherein an increase in input power does not necessarily result in a efficient increase in flow as air drawn within the blower inlet 20 is choked as the air passes through the vanes 64, 66.

Advantageously, the vane height as utilized in the impeller 56 of the present invention has been optimized to provide a pressure at the blower outlet 22 of between about 5 to 20 cm $H_2O$ at an optimal flow rate of 60 liters per minute (LPM). However, the blower assembly 10 may be configured to generate the above-mentioned pressure output at up to 120 LPM in certain cases. The pressure and flow output resulting from the optimized vane height is attainable at an input power of only about 15 watts at the motor assembly 30. Furthermore, such flow characteristics are attainable by the blower assembly 10 which has a reduced size and is of relatively small height and relatively small motor diameter (i.e., approximately 2 inches).

In addition, due to its operating efficiency and minimal creation of noise, vibration and heat, the blower assembly 10 is well-suited for use in breathing devices that must be capable of operating in sensitive environments. For example the blower assembly 10 is specifically suitable for use in a breathing device configured as a CPAP device 126 as may be used to treat obstructive sleep apnea (OSA). In this regard, due to its small size and minimal output of heat, noise and vibration, the blower assembly 10 is suitable for use in a wearable CPAP device 126 as well as in conventional bedside and/or table-top arrangements.

In another aspect of the invention described with reference to FIG. 6, the blower assembly 10 is specifically configured to maintain a close-fitting relation of the impeller 56 to the housing interior surface 26 at impeller 56 speeds of up to 35,000 RPM. More particularly, the free edge 68 of each one of the vanes 64, 66 defines an air gap 76 with the housing interior surface 26. The impeller 56 and bearing assembly 86 are specifically configured such that the air gap 76 is maintained at less than approximately 0.0006 inches during rotation of the impeller 56 and, more preferably, is maintained at approximately 0.0002 inches. The close-tolerance relationship of the vanes 64, 66 to the housing interior surface 26 improves the operating efficiency of the impeller 56 by minimizing vane-to-vane leakage as the air passes from the blower inlet 20 to the blower outlet 22.

In FIG. 7, the blower assembly 10 is shown in an alternative configuration which is functionally and structurally similar to that described above with the exception of differences in the impeller 56 configuration. The arrangement shown in FIG. 7 is also similar to that which is illustrated and disclosed in commonly-owned PCT Publication No. WO2005/091469 having an international filing date of Dec. 16, 2004. However, the impeller 56 configuration illustrated in FIG. 7 omits the downwardly extending lip portion 72 illustrated in the blower assembly 10 of FIG. 6. As will be described in greater detail below, the lip portion 72 facilitates precision balancing of the blower assembly 10 which minimizes vibration output of rotating components and which also improves the compressive efficiency of the impeller 56.

Facilitating the close-fitting relationship between the impeller 56 and the housing interior surface 26 is the oversized bearing assembly 86 mountable within the stator bore 38. The tight tolerances between the impeller 56 and the housing interior surface 26 are also further assisted by the biasing member (e.g., wave spring) described above and which is located adjacent the lower bearing 90. The biasing element 100 compensates for thermal expansion and contraction which occurs during normal operation of the motor assembly 30. The biasing element 100 also compensates for thermal changes resulting from compression of air within the annular chamber 24 by the impeller 56. In this regard, the biasing element 100 is configured to maintain the air gap 76 over the operating life of the blower assembly 10 and does so without altering the bearing load (i.e., the load on the upper and lower bearings 88, 90).

Further assisting in maintaining the air gap 76 is the precision with which the impeller 56 is fabricated. In this regard, accurate static and dynamic balancing of the impeller 56 is facilitated by removal of portions of material from the downwardly-turned ring portion of the impeller 56. As best seen in FIG. 6, the ring portion extends about a perimeter of the ramp portion 70 and is configured to fit within an annular undercut 36 formed along an upper perimeter edge of the stator housing 34. The annular undercut 36 and lip portion 72 of the impeller 56 collectively form a narrow lip gap 74 which allows the outer surface of the lip portion 72 to lie generally flush with the outer surface of the stator housing 34. Such flush arrangement facilitates unobstructed flow of the compressed air from the vanes 64, 66 to the annular chamber 24 of the blower housing 12.

The improvements in operating efficiency as a result of the generally close-fitting air gap 76 and the optimized vane 64, 66 height reduces overall power consumption of the blower assembly 10 such that a breathing device (i.e., a CPAP device 126) using the blower assembly 10 can be operated for extended periods of time using only battery power. For example, at a pressure of 10 cm $H_2O$, a blower assembly 10 as described herein is capable of operating for up to 12 hours. An increased pressure setting (e.g., 12 cm $H_2O$) results in a proportional decrease in battery life. The minimal air gap 76 and precision impeller 56 also reduces vibration which could otherwise be transmitted to the blower device and/or could be radiated outwardly as noise that ultimately may be sensed by the patient. As such, the relatively low amounts of vibration, heat and noise generated by the blower assembly 10 improves patient comfort and therefore enhances the likelihood that devices incorporating the blower assembly 10 will improve patient compliance with prescribed CPAP therapy.

Figure 3:
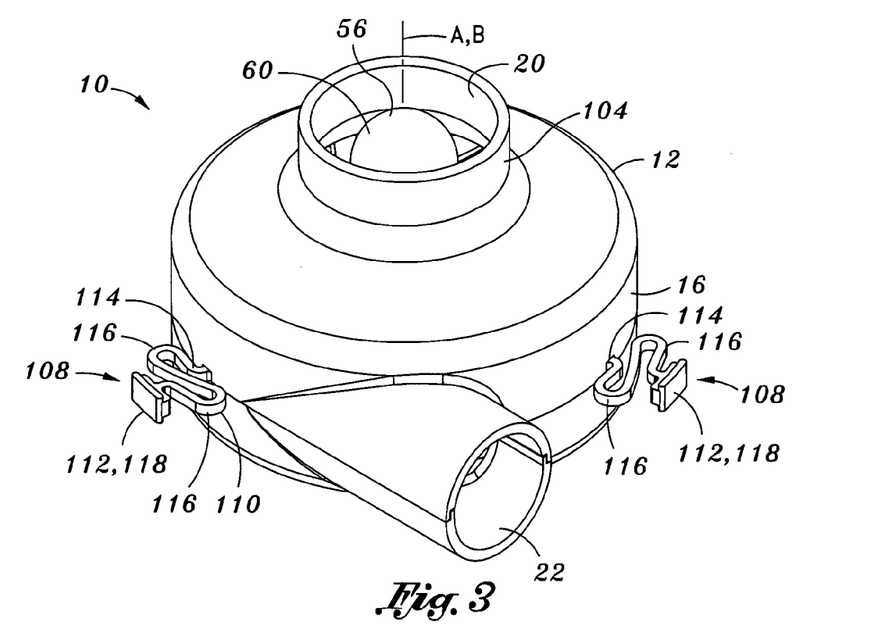
FIG. 3 is a perspective view of the blower assembly in an assembled state.

Referring particularly now to FIGS. 3-5, the blower housing 12 preferably includes at least one and, more preferably, three angularly spaced suspension mounts 108 extending outwardly laterally from the blower housing 12. Although three suspension mounts 108 are shown, any number can be provided and in any configuration or combinations thereof. The suspension mounts 108 are specifically sized and configured to support the blower assembly 10 while attenuating or dampening vibration such as radial and/or axial vibration which may be generated by the blower assembly 10 during rotation of the impeller 56. The suspension mounts 108 are mountable on at least one of the upper and lower housing portions 14, 16 adjacent to the perimeter joint 18. The suspension mounts 108 act as vibration isolators which prevent the majority of vibration generated at the impeller 56 from propagating to outside walls and/or which may be transmitted to the breathing device (e.g., the CPAP device 126).

The suspension mount 108 as described herein represents an improvement in conventional blower and motor vibration isolation systems. For example, commonly-owned U.S. Publication No. 2006/0213516 entitled Portable Continuous Positive Airway Pressure System, the entire contents of which is incorporated by reference herein, discloses a set of foam pads or rubber standoffs which are provided as a means for mechanically isolating the blower assembly 10 from the structure to which the blower assembly 10 is mounted.

Figure 8:
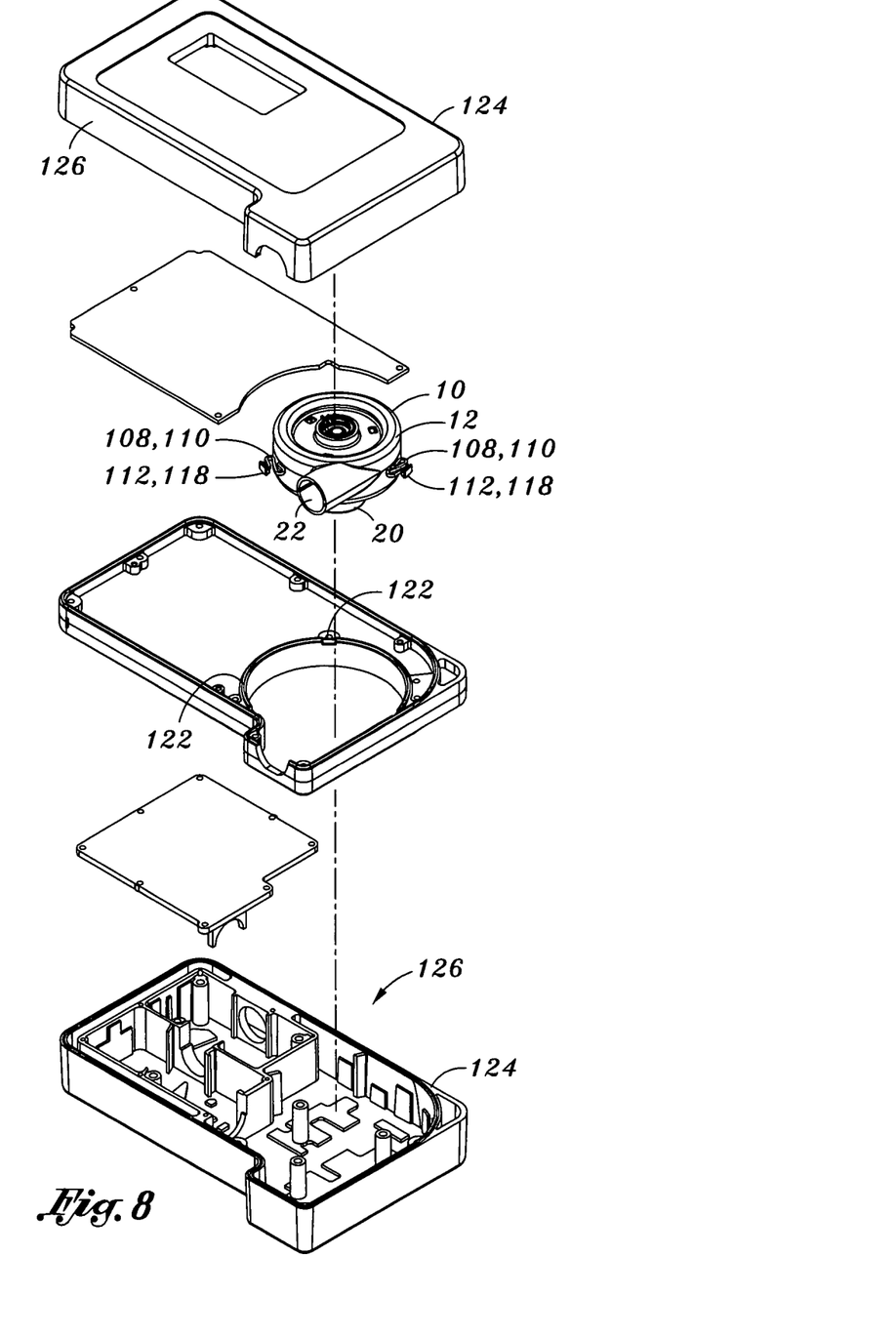
FIG. 8 is an exploded perspective view of the blower assembly as may be mounted in a mounting frame such as that of a continuous positive airway pressure (CPAP) device.
Figure 9:
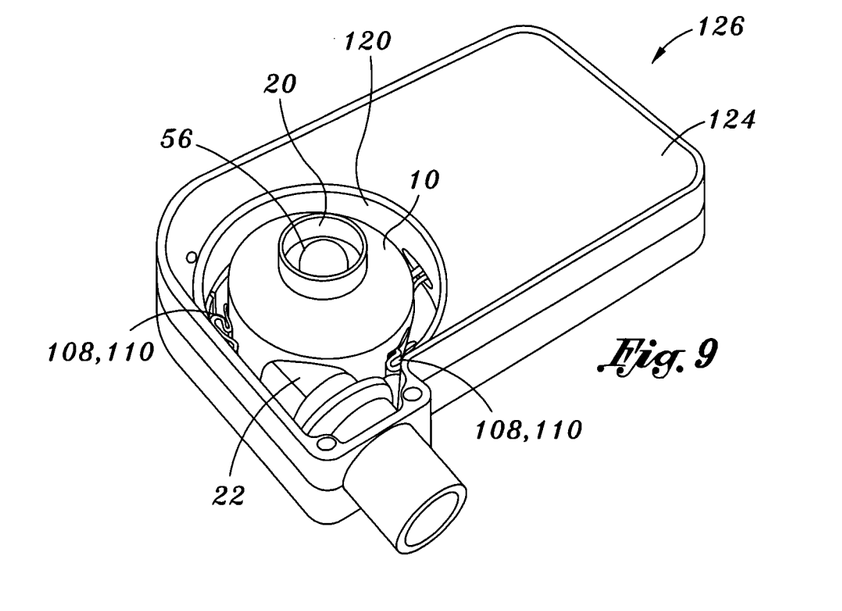
FIG. 9 is a perspective view of the CPAP device and illustrating the blower assembly supported thereon by the suspension mounts.
Figure 10:
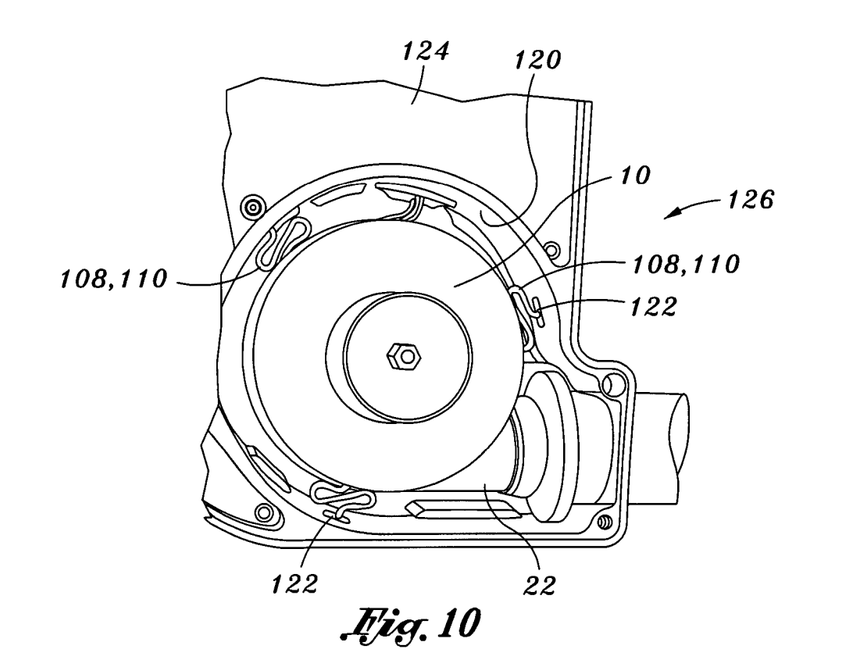
FIG. 10 is an enlarged partial perspective view of the blower housing and illustrating the suspension mounts engaged to the mounting frame of the CPAP device.

Referring particularly to FIG. 5, the suspension mount 108 may be configured as a generally serpentine-shaped spring member 110 which has a free or terminus end 112 adapted to interconnect or mount the blower assembly 10 to a mounting frame 120. For example, as illustrated in FIGS. 8-10, the CPAP device 126 into which a blower assembly 10 may be mounted may include mounting frame 120 which may be provided with a plurality of mounting slots 122. The mounting slots 122 may be axially oriented in order to receive or engage the corresponding one of the terminus ends 112 of the spring member 110. Due to sizing (e.g., cross sectional size and shape) of the spring member 110 in proportion to the configuration of the blower assembly 10 (e.g., mass or natural frequency), transmission of vibration from the blower assembly 10 to the mounting frame 120 is minimized.

In an exemplary embodiment illustrated in FIGS. 8-10, the blower assembly 10 may be mounted in the mounting frame 120 of the housing of the CPAP device 126 in a manner disclosed in U.S. Publication No. 2006/0213516, mentioned above. More specifically, the mounting frame 120 of the CPAP device 126 may include a plurality of axially-oriented mounting slots 122 which are sized and configured to receive a corresponding mounting portion of the spring member 110. As can be seen in FIG. 3, each of the terminus ends 112 of the spring members 110 includes a generally axially oriented tab member 118 which is sized and configured to mate with the mounting slot 122.

The suspension mount 108 is preferably integrally formed with one of the upper and lower housing portions 14, 16 such as by injection molding. Each one of the serpentine spring members 110 extends laterally outwardly from the blower housing 12 and immediately forms a 90° bend 114. The suspension mount 108 may further include a pair of 180° bends 116 before terminating at a further 90° bend 114 at the free end of the spring member 110. However, any number of turns in the spring member 110 may be included in order to provide the desired damping or attenuating characteristics. Furthermore, the tab member 118 may be further sized and configured in proportion to the mass and natural frequency of the blower assembly 10.

Also provided is a method of constructing a blower assembly 10. With reference to FIGS. 1-6, the method comprises the steps of forming the stator assembly 32 having a plurality of angularly spaced core sections 42 which extend radially outwardly from the bearing carriers 92, 94. As was earlier mentioned, each one of the core sections 42 has a winding 44 extending therearound and which is sequentially magnetizable by the application of current thereto. The upper and lower bearing carriers 92, 94 may be integrally formed with or molded with the stator assembly 32 as a unitary structure. The stator housing 34 is preferably integrally molded with the lower housing portion 14 by supporting the stator assembly 32 in its component parts in a suitable injection mold after which polymeric material such as a suitable thermoplastic (e.g., polycarbonate material) is injected in order to form the combination lower housing portion 14 and stator assembly 32.

Position sensors 48 such as Hall sensors may be formed with the stator assembly 32 as illustrated in FIG. 4. Housing apertures 40 may further be included with the stator assembly 32 in order to control thermal shrinkage during cooling of the stator assembly 32 after injection molding and therefore better maintain dimensional control of the blower assembly 10. However, it should be noted that the stator assembly 32 and its electrical components may be formed as separate components from the lower housing assembly and may be thereafter secured together by any suitable means such as by sonic welding, adhesive bonding or mechanical fastening.

Importantly, the stator housing 34 is molded such that the stator housing 34 encapsulates the stator assembly 32 and confines or affixes the upper and lower bearing carriers 92, 94. The stator bore 38 defines the stator axis A and is formed in the stator housing 34 such that the stator bore 38 is coaxially aligned with the upper and lower bearing carriers 92, 94. The motor shaft 78 may be formed with the shaft shoulder 84 disposed on the distal end 80 thereof. The rotor magnet 106 is preferably fixably mounted to the motor shaft 78 such that the rotor magnet 106 is disposed in abutting contact with the shaft shoulder 84. Assembly of the motor shaft 78 includes installation of the spacer 96 ring followed by mounting of the upper bearing 88.

Figure 2:
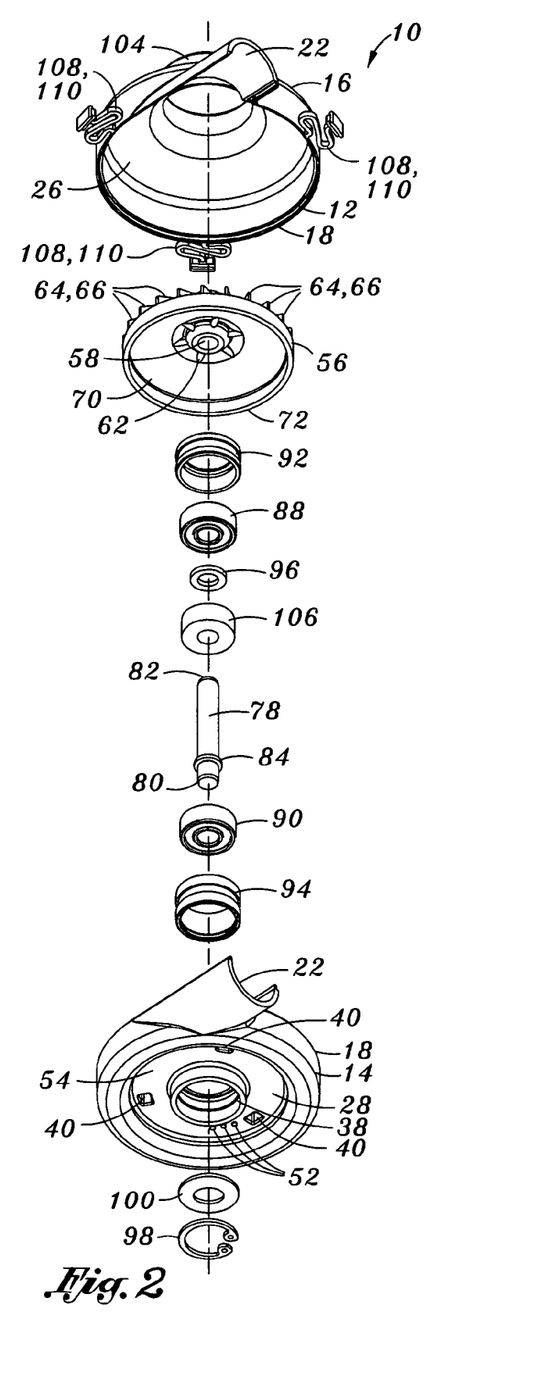
FIG. 2 is a perspective exploded view looking in an upward direction at the blower assembly and illustrating a retainer element for removably retaining a bearing assembly and rotor magnet within a stator assembly of the motor assembly.

The combination upper bearing 88, spacer 96 element and rotor magnet 106 are then insertable into the stator bore 38 from an underside of the blower assembly 10 as best seen in FIG. 2. The lower bearing 90 is preferably installed on the motor shaft 78 in abutting contact with an underside of the shaft shoulder 84. The biasing element 100 (e.g., spring washer) and retainer element 98 (e.g., snap ring) are then installed within the lower housing flange 102. The impeller 56 may be mounted on the proximal end 82 of the motor shaft 78 such as by press fit until a mounting boss 62 of impeller 56 is placed in abutting contact with the upper bearing 88. The PCB 54 and other electronic connecting components may be mounted to the underside of the lower housing portion 14 as shown in FIG. 4.

As was earlier mentioned, the impeller 56 is formed such that the vane height is optimized to allow production of a flow rate at the blower outlet 22 of up to approximately 125 LPM at a pressure of up to approximately 20 cm $H_2O$ using less than approximately 15 watts of input power at the motor assembly 30. In addition, the coaxial alignment of the stator axis A with the shaft axis B is such that an air gap 76 between the free edges 68 of the vanes 64, 66 and the housing interior surface 26 is maintained at less than approximately 0.0006 inches during rotation of the impeller 56. The air gap 76 is maintained by precision static and dynamic balancing of the impeller 56 such as by selectively removing portions of the lip portion 72 of the impeller 56.

The description of the various embodiments of the present invention is presented to illustrate preferred embodiments thereof and other inventive concepts may be otherwise variously embodied and employed. The appended claims are intended to be construed to include such variations except insofar as limited by the prior art.

What is claimed is:

1. A blower assembly comprising:
   a blower housing;
   a motor assembly disposed within the blower housing and including a stator assembly and a rotor magnet;
   an impeller rotatable with the motor assembly; and
   at least one suspension mount extending laterally outwardly from a perimeter of the blower housing and being sized and configured to support the blower assembly, the suspension mount integrally formed with the blower housing by injection molding.

2. The blower assembly of claim 1 wherein:
   the motor assembly is configured as a three-slot/two-pole brushless D.C. motor;
   the stator assembly including a stator bore extending therethrough;
   the rotor magnet being rotatable within the stator bore.

3. The blower assembly of claim 1 wherein the suspension mount is configured to attenuate vibrations generated during rotation of the impeller.

4. The blower assembly of claim 1 wherein the suspension mount is configured as a serpentine spring member.

5. The blower assembly of claim 4 wherein the suspension mount comprises three of the serpentine spring members angularly spaced about the perimeter of the blower housing.

6. The blower assembly of claim 5 wherein:
   the blower assembly is adapted to be mounted on a mounting frame having at least one mounting slot;
   the spring member having a free end sized and configured to be engaged to the mounting slot.

7. The blower assembly of claim 1 wherein:
   the blower housing includes upper and lower housing portions engageable to one another at a perimeter joint;
   the suspension mount extending outwardly from at least one of the upper and lower housing portions and being positioned adjacent to the perimeter joint.

* * * * *